United States Patent [19]
Cianci et al.

[11] Patent Number: 5,313,121
[45] Date of Patent: May 17, 1994

[54] CIRCUIT FOR PROCESSING SIGNALS SUPPLIED BY A ZIRCONIUM-TYPE OXYGEN SENSOR

[75] Inventors: Cesario Cianci, Pianezza; Franco Salerno, Alpignano, both of Italy

[73] Assignee: Marelli Autronica S.p.A., Milan, Italy

[21] Appl. No.: 807,513

[22] Filed: Dec. 16, 1991

[30] Foreign Application Priority Data

Dec. 27, 1990 [IT] Italy .................... 68063 A/90

[51] Int. Cl.$^5$ .................... G06G 7/12; H03K 5/13
[52] U.S. Cl. .................... 307/494; 307/608
[58] Field of Search .......... 307/490, 494, 355, 261, 307/608, 252, 253

[56] References Cited

U.S. PATENT DOCUMENTS

| | | | |
|---|---|---|---|
| 4,716,306 | 12/1987 | Sato et al. | 307/494 |
| 4,749,955 | 6/1988 | Cook | 330/253 |
| 4,801,827 | 1/1989 | Metz | 307/608 |
| 4,812,780 | 3/1989 | Zimmerman | 330/253 |
| 5,051,628 | 9/1991 | Hanna | 307/355 |
| 5,113,090 | 5/1992 | Imaizumi et al. | 307/494 |

OTHER PUBLICATIONS

IEEE Journal of Solid-State Circuits, vol. SC-16, No. 6, Dec. 1981, pp. 677–681, N.Y., USA-B. D. Miller et al: "Instrumentation amplifier IC designed for oxygen sensor interface requirements".

IEEE Transactions on Circuits and Systems, vol. CAS-32, No. 11, Nov. 1985, pp. 1097–1104, N.Y., USA-R. R. Torrance et al: "CMOS Voltage to Current Transducers".

IEEE Journal of Solid-State Circuits, vol. 25, No. 2, Apr 1990, pp. 546–554, N.Y., USA-L. Tomasini et al: "A fully differential CMOS line driver for ISDN".

*Primary Examiner*—Jin F. Ng
*Assistant Examiner*—Sinh Tran
*Attorney, Agent, or Firm*—Sughrue, Mion, Zinn, Macpeak & Seas

[57] ABSTRACT

The circuit includes a differential voltage/current converter (V/I) for connection to the sensor (S), a differential transresistance amplifier (TDA) whose inputs are connected to the outputs of the converter (V/I), and a double-ended/single-ended converter (D/S) connected to the outputs of the amplifier (TDA). The circuit is conveniently formed as an integrated circuit by CMOS P-well technology.

7 Claims, 5 Drawing Sheets

CIRCUIT FOR PROCESSING SIGNALS SUPPLIED BY A ZIRCONIUM-TYPE OXYGEN SENSOR

BACKGROUND OF THE INVENTION

The present invention relates to a circuit for processing signals supplied by a zirconium-dioxide oxygen sensor or lambda probe, particularly for use as an interface circuit between such a sensor and an electronic control unit in a system for controlling the emissions of an internal combustion engine for motor vehicles.

More specifically, the invention concerns a circuit including a voltage/current converter with two input terminals for connection to the terminals of the oxygen sensor and an amplifier circuit connected to the output of the converter.

A circuit of this type is constituted by the integrated device LM1964 which is produced and marketed by National Semiconductors. The structure of this known device is described in the article "Instrumentation Amplifier ICs Designed for Oxygen Sensor Interface Requirements" by B. D. Miller and L. R. Sample, IEEE Journal of Solid-state Circuits, Vol. SC-16, No. 6, December 1981.

The known circuit described in this article includes a voltage/current converter in which the input signal from the sensor is processed differentially but the voltage/current conversion is carried out non-differentially with an open loop so that errors which depend on the integration process in the circuit (current and offset bias errors, transistor amplification, Early effect) are introduced. The voltage/current converter is connected to a non-inverting amplifier which further amplifies the errors introduced during the conversion. The amplification characteristics of the integrated circuit LM1964 therefore depend not only on the ratio between the resistances of some resistors, but also on the "matching" of the active components. The device, which has seven terminals or pins for external connections, thus has a good twenty terminals or pins altogether, thirteen of which serve for the calibration of the characteristics of internal generators, the offsets and the gains. The device is expensive and delicate because of the numerous calibration operations needed. Moreover, it requires two different supply voltages (+5 and +12V).

SUMMARY OF THE INVENTION

The object of the present invention is to provide a circuit of the type indicated above which solves the problems of the prior circuit considered above.

According to the invention, this object is achieved by a processing circuit of the type specified above, characterised in that:

the voltage/current converter is differential and has two output terminals which, in operation, output two equal and opposite currents whose intensity is proportional to the voltage between the inputs of the converter, and that the amplifier circuit is a high-gain, differential transresistance amplifier having two inputs connected to the outputs of the converter and two output terminals between which there is a differential voltage proportional to the intensity of the currents output by the converter in operation.

A double-ended/single-ended conversion circuit may conveniently be connected to the outputs of the amplifier.

The circuit according to the invention can operate in connection with a balanced, single-ended or semi-differential sensor.

Conveniently, the circuit according to the invention may be formed as an integrated circuit by CMOS P-well technology.

The differential voltage/current converter may, to advantage, be formed with a differential input stage having N-channel CMOS P-well transistors with their sources connected to their P-wells, the sources of the transistors constituting the inputs of the converter. This solution enables the circuit to process signals which become negative with respect to earth without the signals being clamped.

BRIEF DESCRIPTION OF THE DRAWINGS

Further characteristics and advantages of the circuit according to the invention will become clear from the detailed description which follows with reference to the appended drawings, provided purely by way of non-limiting example, in which.

DESCRIPTION OF A PREFERRED EMBODIMENT

Figure 1:
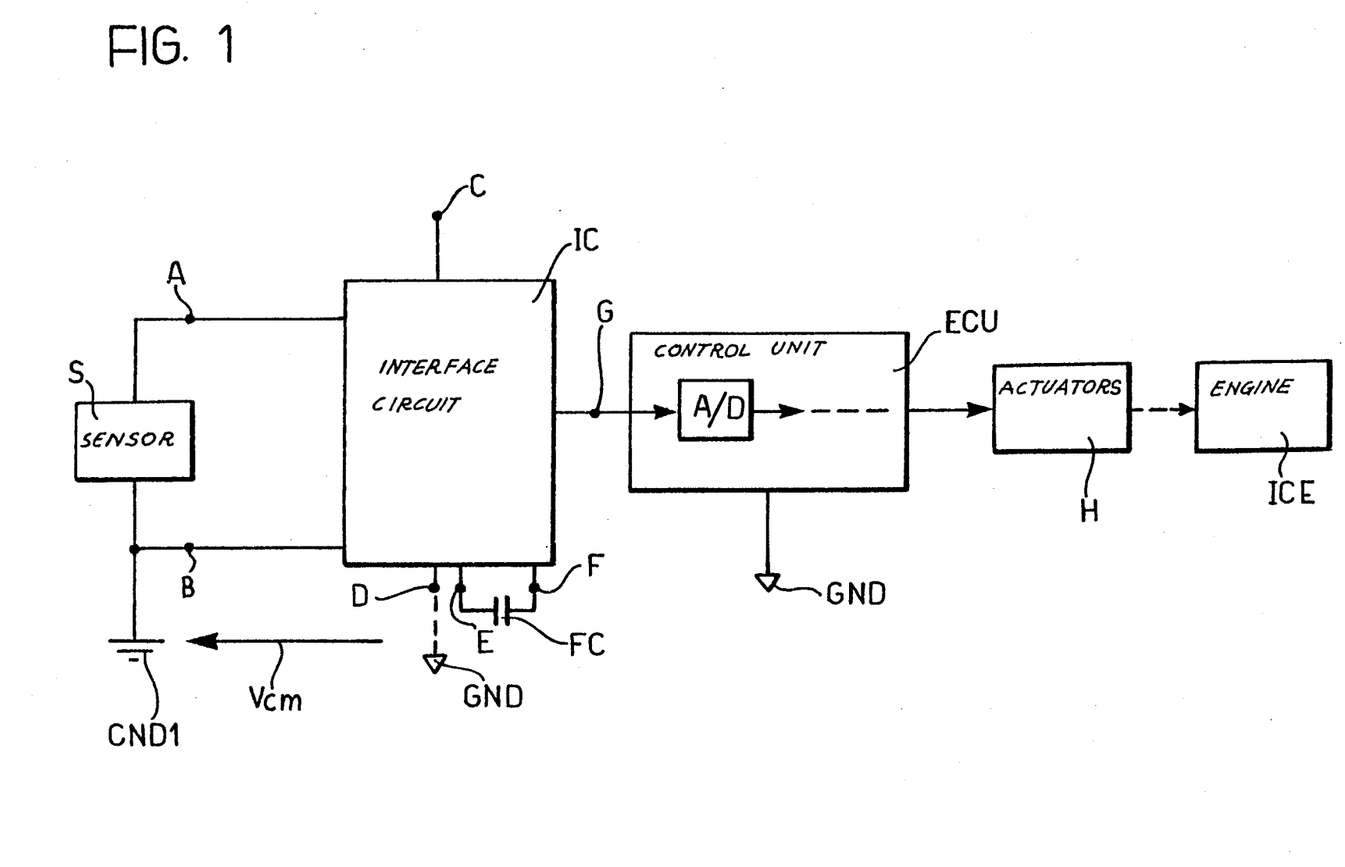
FIG. 1 is a block diagram showing the structure of a system for controlling the emissions of an internal combustion engine, including a zirconium-dioxide oxygen sensor and a circuit according to the invention.

FIG. 1 is a diagram of a system for controlling the emissions of an engine. The system includes, in known manner, a zirconium-dioxide oxygen sensor S also currently known as a lambda probe. Essentially, this sensor is an electrochemical cell which is sensitive to the difference between the oxygen content of the atmosphere and that of the exhaust gases of the engine. From an electrical point of view it can be considered essentially to generate a voltage which varies in dependence on temperature and on the ratio between the partial pressures of the oxygen in the atmosphere and in the exhaust gases.

In the system of FIG. 1, the sensor S is connected to an electronic control unit ECU by means of an interface circuit IC. This circuit has two input terminals, indicated A and B, which are connected to the terminals of the sensor S, two terminals C and D for connection to a voltage supply $V_{dd}$ and to earth, two further terminals E and F for connection to a filter capacitor CF, and an output terminal G typically for connection to an analog/digital converter A/D of the control unit ECU.

Very briefly, in operation, the interface circuit amplifies and filters the signal supplied by the sensor and then passes the amplified and filtered signal to the control unit ECU. This unit, which may typically be formed with the use of a microprocessor, correspondingly drives actuators H of known type associated with the internal combustion engine ICE. In particular, these actuators are adapted to modify the air/fuel ratio or the richness of the mixture supplied to the internal combustion engine.

Typically, the sensor S is mounted at a certain distance from the interface circuit IC and is connected to earth at the engine, indicated GND1 in FIG. 1. The interface circuit IC and the unit ECU, however, are connected to another earth conductor, indicated GND in FIG. 1. The input of the interface circuit IC is consequently affected not only by the signal actually coming from the sensor S but also by a common-mode voltage error $V_{mc}$ represented by the potential difference between the earth GND1 and the earth GND. This potential difference may assume quite significant values, of the order of +1V.

The interface circuit IC also has to be able to function when the connection between one or other of the terminals of the sensor and the circuit is broken. In these circumstances, the circuit IC must continue to operate and supply the unit ECU with a signal having characteristics which enable the fault to be diagnosed.

Figure 2:
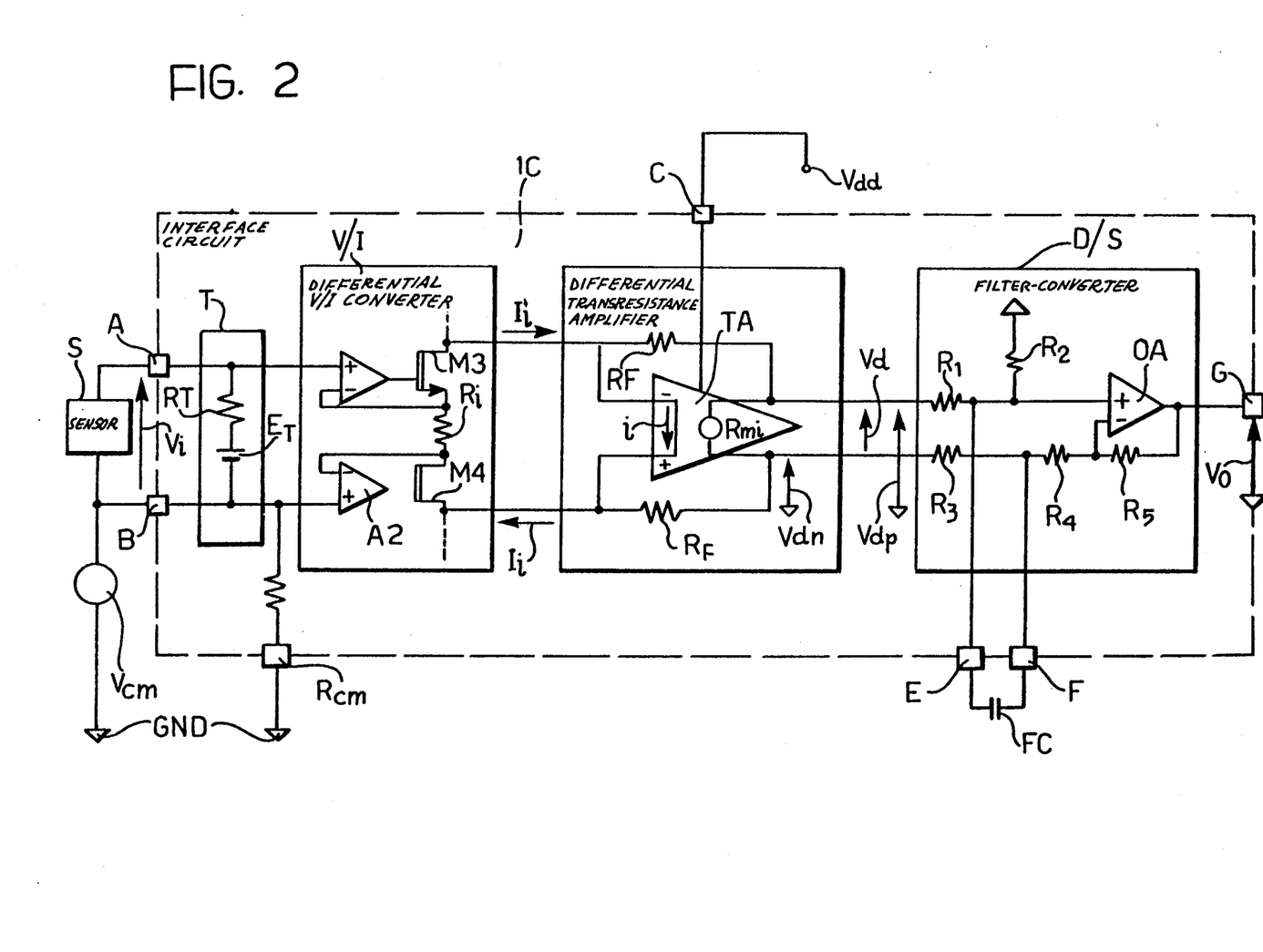
FIG. 2 is a diagram of the internal structure of the circuit according to the invention for processing the signals supplied by an oxygen sensor.

FIG. 2 shows a notional structure of an interface circuit IC according to the invention. In this drawing only the earth conductor GND is shown; the common-mode voltage error $V_{cm}$ is taken into account by means of a generator for generating a notional voltage, indicated $V_{cm}$, between the sensor S and the earth GND.

As shown in FIG. 2, an interface circuit according to the invention includes basically a differential voltage/current converter V/I with two inputs connected to the terminals A and B respectively (and hence to the sensor S) and two outputs which are connected respectively to two inputs of a differential transresistance amplifier, generally indicated TDA. This amplifier has two outputs connected to the inputs of a circuit D/S which performs the functions of a double-ended/single-ended converter and a filter. The filter capacitor FC is connected to this circuit.

The output of the circuit D/S in fact represents the output of the entire interface circuit.

Essentially, the differential voltage/current converter V/I includes two input amplifiers A1 and A2 whose outputs are connected to the gates of two transistors M3 and M4. Conveniently, these are CMOS transistors. As will be appreciated better from the following, the entire interface circuit IC can conveniently be produced in the form of a CMOS P-well integrated circuit with a single supply voltage of 5V.

A resistor $R_i$ is interposed between the sources of the transistors M3 and M4. The drains of M3 and M4 represent the outputs of the converter V/I and are connected to the inputs of the differential transresistance amplifier TDA.

If the voltage generated by the sensor S is indicated $V_i$, in operation, the converter V/I outputs two current signals with opposite signs but the same intensity $I_i = -V_i/R_i$.

Essentially, the amplifier TDA comprises a transresistance amplifier TA with two feedback resistors $R_F$ between its inputs and outputs.

If the current flowing between the inputs of the amplifier TA is indicated i, in operation, this amplifier outputs a differential voltage signal $V_d = R_m \cdot i$ in which $R_m$ is the gain (transresistance) of the amplifier.

With reference to FIG. 2, it can easily be seen that the differential voltage output by the amplifier TDA is expressed by the following equation:

$$V_d = 2 \times (V_i/R_i) \times R_m/(1 + R_m/R_F)$$

If the transresistance $R_m$ of the amplifier TA is quite high and, in particular, much greater than $R_F$, the equation for the voltage $V_d$ is reduced to the following:

$$V_d = 2 \times V_i \times (R_F/R_i)$$

This equation shows that, if the transresistance gain of the amplifier TA is high enough, in practice, the overall gain $V_d/V_i$ depends solely on the ratio between the resistances $R_F$ and $R_i$. It is possible, by usual integration techniques, to form the resistances in such a way that the ratio between them is precisely 1%, without the need for external calibration. The interface circuit IC according to the invention can thus conveniently be produced in the form of an integrated circuit with only seven pins and a single supply (e.g. +5V), that is, with only the seven terminals indicated A to G in FIGS. 1 and 2, without the need for further pins for internal calibration. This is a substantial advantage of the solution according to the invention.

The signal $V_d$ is applied to the input of the converter D/S. This converter includes an operational amplifier OA with its non-inverting input connected to an output of the differential transresistance amplifier TDA by means of a resistor $R_1$. A resistor $R_2$ is connected between the non-inverting input of the amplifier OA and earth GND.

The inverting input of OA is connected to the other output of TDA by means of two resistors $R_3$ and $R_4$.

A feedback resistor $R_5$ is connected between the inverting input and the output of OA.

The terminals E and F are connected respectively to the junction between $R_1$ and $R_2$ and the junction between $R_3$ and $R_4$.

If the voltages between the outputs of TDA and earth GND are indicated $V_{dp}$ and $V_{dn}$, the equation for the voltage $V_0$ output by the conversion and filtering circuit D/S is as follows:

$$V_0 = V_{dp} \times [R_2/(R_1+R_2)] \times [1 + R_5/(R_3+R_4)] - V_{dn} \times [R_5/(R_3+R_4)]$$

If the circuit D/S is formed in such a way that:

$$R_1 = R_2 = R_3 = R_4 = R \text{ and } R_5 = 2R,$$

then $$V_0 = V_{dp} - V_{dn} = V_d$$

Since the resistor $R_2$ is connected to earth, the output characteristic of the circuit D/S is such that the output voltage is 0 when the differential signal $V_d$ is zero.

The capacitor FC, which is outside the interface circuit IC, determines the low-pass filter characteristic of the overall transfer function $V_0/V_i$, short-circuiting the input of the output amplifier OA at a frequency $F_p = \frac{1}{2} \pi (R\ C_{FC})$, in which $C_{FC}$ is the capacitance of the capacitor FC.

A circuit, generally indicated T, for generating a reference voltage is connected between the input terminals A and B. This circuit enables the device as a whole to operate even if the sensor is disconnected from the input A of IC and, in the schematic embodiment shown in FIG. 2, it comprises essentially a resistor $R_T$ in series with a voltage generator $E_T$ which is adapted to generate a voltage of the order of, for example, 500 mV. The resistance of the resistor $R_T$ must be much greater than the internal resistance of the sensor S so that, when the sensor is actually connected to the terminal A, the circuit T has practically no effect.

When the sensor S has to be disconnected from the terminal A, however, the circuit T causes the output voltage $V_o$ to assume a predetermined constant value.

The diagram of the circuit T shown in FIG. 2 is purely theoretical. In practice, the function of the generator $E_T$ is performed by current generators according to a measure already used in the integrated device LM1964 and described in the article mentioned in the introduction to the present description.

In FIG. 2, a resistor, indicated $R_{cm}$, is interposed between the terminals B and D for polarising the circuit IC when its input is completely balanced.

Although the resistor $R_{cm}$ is shown within the circuit IC in the diagram of FIG. 2, clearly, it could also be outside that circuit between the terminal D and earth GND.

Figure 3:
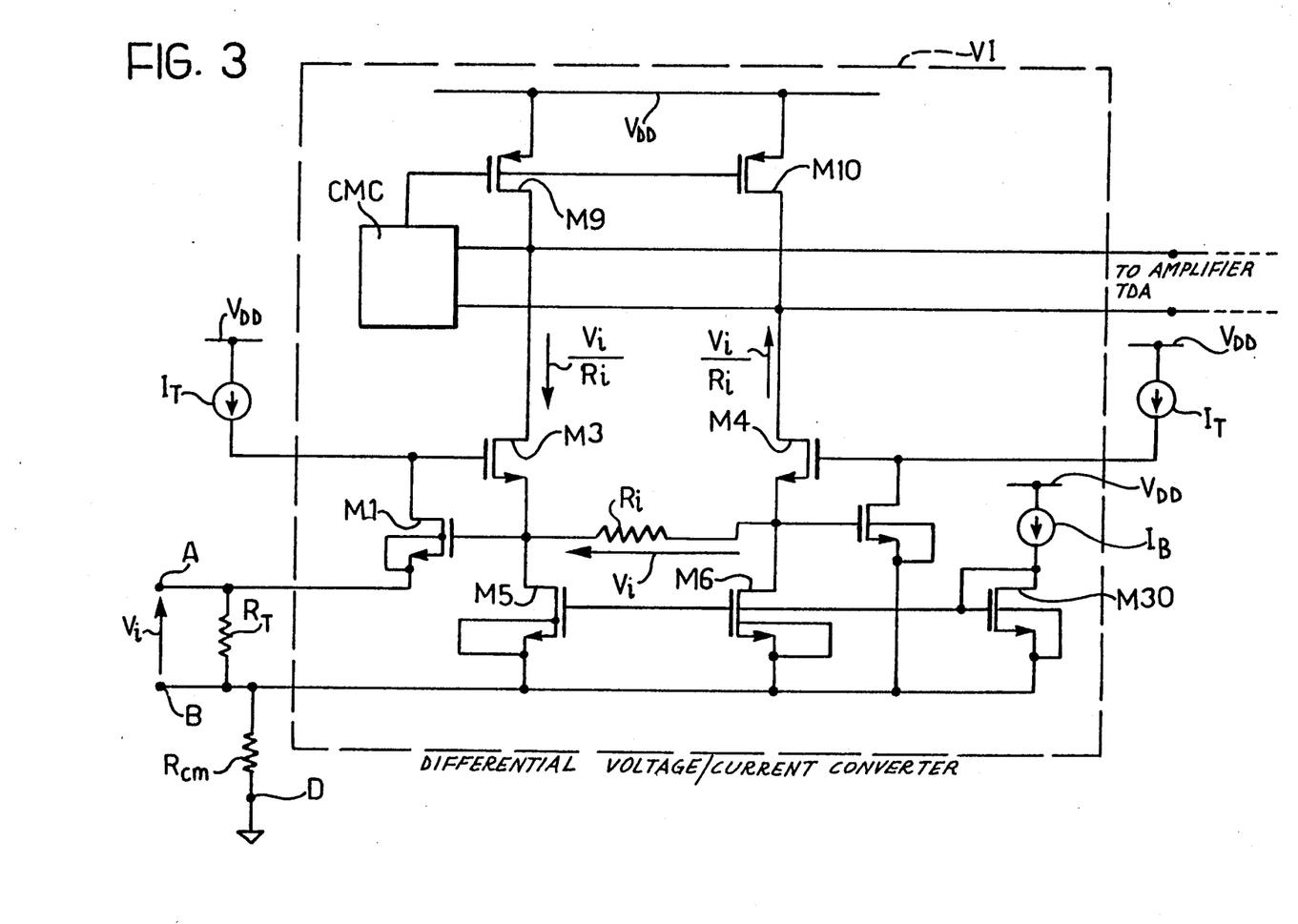
FIG. 3 is a circuit diagram of an embodiment of a differential voltage/current converter included in the circuit of FIG. 2.

In the embodiment shown in FIG. 3, the differential converter V/I includes two N-channel CMOS P-well input transistors M1 and M2 having their source terminals connected to their P-wells and to the terminals A and B. The gates of M1 and M2 are connected respectively to the drains of another two N-channel CMOS P-well transistors M5 and M6 which operate as current generators, their sources and P-wells being connected to the terminal B. The drains of M5 and M6 are connected to the source terminals of M3 and M4, whose gates are connected to the drains of M1 and M2.

The resistor $R_i$ is connected between the sources of M3 and M4.

The gates of M5 and M6 are connected to each other and to the gate of a further transistor M30, also of the N-channel CMOS P-well type, having its source connected to its P-well and to the terminal B and its drain connected to its gate. A current generator for generating a current of intensity $I_B$ is connected to the drain of M30.

The connection of the sources of M5 and M6 to the terminal B ensures that M5 and M6, which generate polarising currents, are always subject to a voltage at least equal to the gate-source voltage of M1 or M2, regardless of the common-mode voltage applied to the input terminals B.

Two generators for generating currents $I_T$ are connected to the drains of M1 and M2. These current generators supply the polarising current to the input transistors M1 and M2 and at the same time cause a voltage drop in the resistor $R_T$ which is functionally equivalent to that induced by the generator $E_T$ in the diagram of FIG. 2.

The transistors M5 and M6 ensure the polarisation of the transistors M3 and M4, enabling negative swings of the common-mode input signal down to a predetermined value which may be, for example, about −5V.

The drains of M3 and M4 are connected to the drains of two further transistors M9 and M10 whose source terminals are connected to the voltage supply $V_{DD}$ and whose gates are connected to each other and to the output of a circuit CMC for controlling the common-mode voltage at the input of the operational amplifier TA. The control circuit CMC has two inputs connected to the drains of M9 and M10.

In summary, the V/I converter operates in the following manner.

As a result of the feedback to the transistors M1 and M2, the input voltage $V_i$ is transferred to the resistor $R_i$, creating a differential imbalance in the drain currents of the transistors M3 and M4. This differential current is collected by the feedback resistors $R_F$ of the differential transresistance amplifier TDA which produces a differential output voltage $V_d$, the equation for which is given above.

The transistors M9 and M10, together with the control circuit CMC, determine the common-mode voltage at the input of the operational amplifier TA in the manner which will now be described further with reference to FIGS. 4 and 5.

Figure 4:
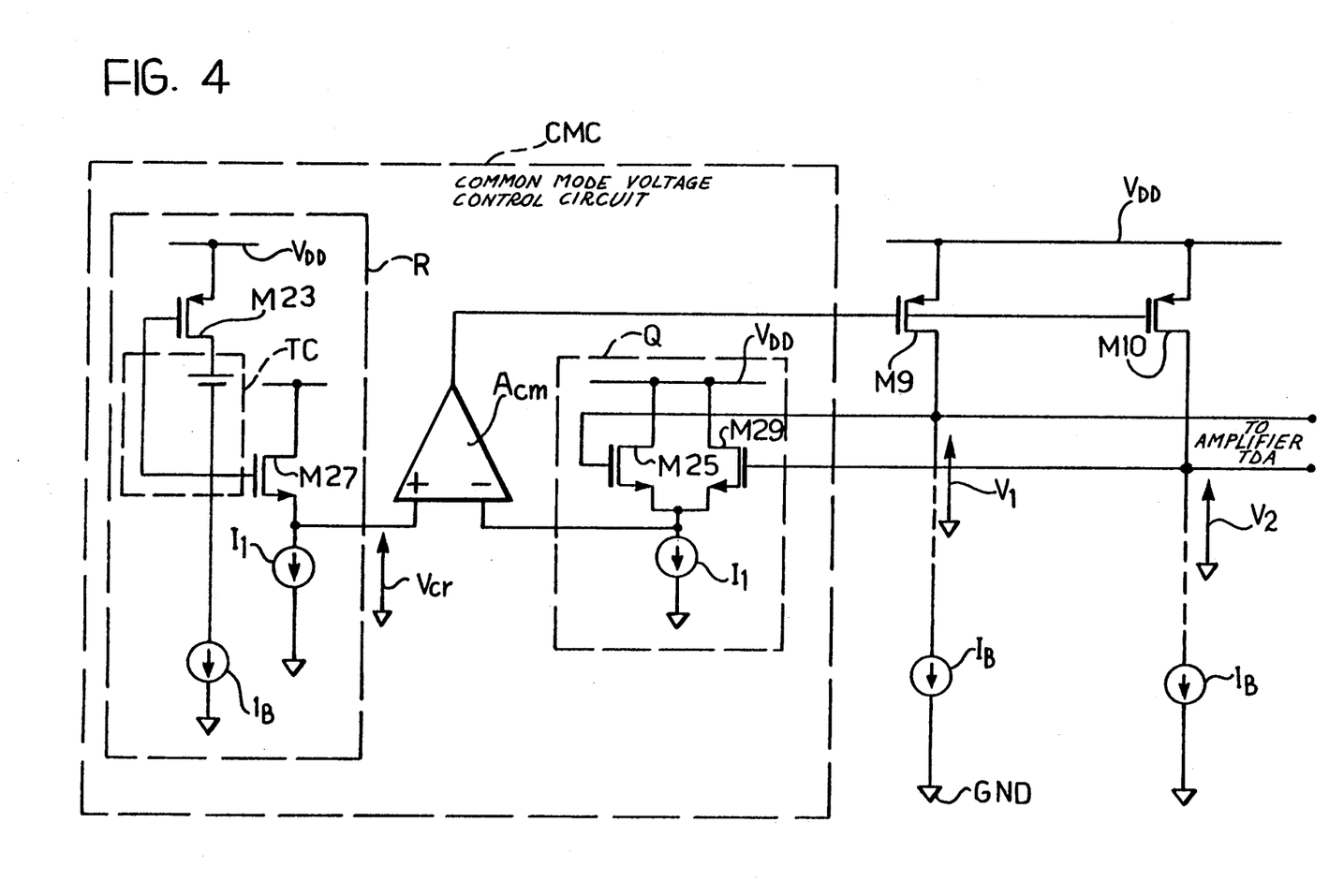
FIG. 4 is a diagram showing an embodiment of a common-mode voltage control circuit included in the circuit of FIG. 3.

As can be seen in FIG. 4, the control circuit CMC includes a circuit Q which is connected to the drains of M9 and M10 to measure the variations in the common-mode voltage $V_{cmi}$ at the input of the amplifier TDA. In the embodiment illustrated, the circuit Q includes two CMOS transistors, indicated M28 and M29, having their gates connected to the drains of M9 and M10, their drains connected to the supply $V_{DD}$, and their sources connected to each other and to a current generator $I_1$.

The sources of M28 and M29 represent the output of the circuit Q, this output being connected to a first input of an amplifier $A_{cm}$ whose output is connected to the gates of M9 and M10. The other input of the differential amplifier $A_{cm}$ is connected to the output of a reference circuit, generally indicated R.

The amplifier $A_{cm}$ and the circuits Q and R together constitute a feedback loop which tends to stabilise the common-mode voltage $V_{cmi}$. The amplifier $A_{cm}$ controls the gates of M9 and M10 so that the voltage between its input terminals tends to be cancelled out.

In order to maximise the dynamics of the input signal $V_i$, the transistors M9 and M10 conveniently operate at the limit of their saturation condition. The circuit CMC therefore imposes a common-mode voltage:

$$V_{cmi} = \tfrac{1}{2} \times (V_1 + V_2) = V_{DD} - V_{dssat}$$

in which $V_1$ and $V_2$ are the voltages of the drains of M9 and M10 with respect to earth GND and $V_{dssat}$ is the saturation drain-source voltage of the transistors M9 and M10.

The reference circuit R generates a corresponding reference voltage $V_{cr}$ which is equal to $V_{DD} - V_{dssat}$. For this purpose, the circuit R includes a first transistor M23 which is a replica of M9 (M10) and a transistor M27 which is a replica of M28 (M29). The source of M23 is connected to the supply $V_{DD}$ and its gate is connected to the gate of M27. The drain of M27 is connected to $V_{DD}$ and its source is connected to a current generator $I_1$.

In the diagram of FIG. 4, a circuit, generally indicated TC, for generating a polarising voltage is interposed between M23 and M27. In the theoretical solution shown in FIG. 4, the circuit TC includes a generator for generating a threshold voltage $V_t$ between the gate of M27 and the drain of M23; moreover, the gates of M23 and M27 are connected to each other and a generator for generating a current $I_B$ is interposed between TC and earth. The generator of the current $I_B$ corresponds to the current generators, also indicated $I_B$, which are shown in FIG. 4 between the drains of M9 and M10 and are equivalent to the circuitry between the drains of those transistors and earth in the diagram of FIG. 3.

The generator of the voltage $V_t$ causes the transistor M23 to be polarised to a saturation voltage equal to the saturation voltage to be imposed on the transistors M9 and M10.

Figure 5:
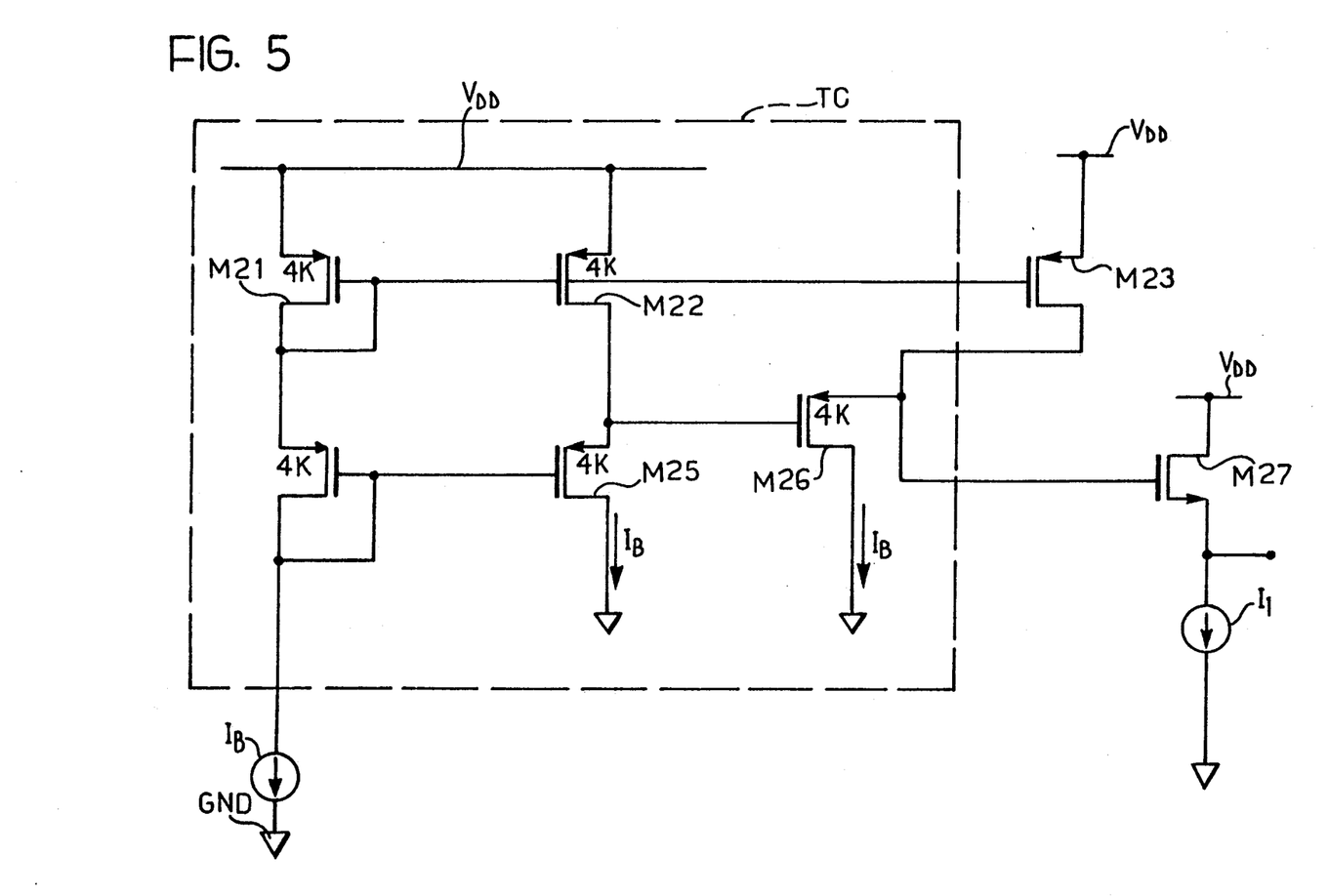
FIG. 5 shows an embodiment of a threshold-voltage generator for the circuit shown in FIG. 4.

FIG. 5 shows an embodiment of the circuit TC of FIG. 4, including five P-channel CMOS P-well transistors indicated M21, M22, M24, M25 and M26. The gates of M21 and M24 are connected to their drains. The source of M21 is connected to the voltage supply $V_{DD}$ and its drain is connected to the source of M24, which in turn has its gate connected to that of M25 and its drain connected to the current generator $I_B$. The source of M22 is connected to $V_{DD}$, its gate is connected to the gate of M21 and its drain is connected to the source of M25. The drain of M25 is connected to earth GND and its source is connected to the drain of M26, whose drain is connected to earth and whose source is connected to the drain of M23. The dimensions of the transistors M21, M22, M25 and M26 are such that they can carry the same current. Moreover, they are assumed to have the same threshold voltage $V_t$. The transistor M24 is formed in a manner such that its aspect ratio $K = W/L$ (W = the width of the channel; L = the length of the channel) is one quarter of those of M21, M22, M25 and M26.

In these circumstances, as can easily be seen, the circuit TC produces a voltage $V = V_{dssat}$ between the source and the drain of M23 in operation.

Naturally, the layout described above with reference to FIG. 5 is only an example of the various ways in which the particular voltage $V = V_{dssat}$ could be produced between the drain and the source of M23.

The circuit according to the invention has numerous advantages.

In the first place, as already seen, the amplification gain, in practice, depends exclusively on the ratio between the resistances of two resistors and can be made sufficiently precise without the need for subsequent external calibration.

As can be seen from FIG. 2, the structure of the circuit is perfectly symmetrical and differential and the device as a whole is highly immune to bias errors (gain, off-set and drift) and has a high input common-mode rejection ratio (CMRR) and power-supply rejection ratio (PSRR).

The circuit can be produced in the form of an integrated circuit with an extremely small number of pins and only one supply voltage. The use of P-well CMOS technology enables the common-mode voltage swings to be limited to very low values.

Naturally, the principle of the invention remaining the same, the forms of embodiment and details of construction may be varied widely with respect to those described and illustrated purely by way of non-limiting example, without thereby departing from the scope of the present invention.

What is claimed is:

1. A circuit for processing signals supplied by a zirconium-dioxide oxygen sensor or lambda probe, particularly for use as an interface circuit between such a sensor and an electronic control unit in an emission control system of an internal combustion engine, the circuit including a voltage/current converter with two input terminals for connection to terminals of the oxygen sensor and an amplifier circuit connected to the output of the converter, wherein the voltage/current converter is differential and has two output terminals which, in operation, output two equal and opposite currents whose intensity is proportional to the voltage between the inputs of the converter, and the amplifier circuit is a differential trans-resistance amplifier with a high gain, having two inputs connected to the two output terminals of the converter and two output terminals between which there is a differential voltage proportional to the intensity of the currents output by the converter in operation;

wherein a double-ended/single-ended conversion circuit is connected to the two output terminals of the amplifier, and wherein the differential voltage-current converter has a differential input stage formed by N-channel CMOS P-well transistors each having its source connected to its P-well, the sources of the transistors acting as inputs for the converter.

2. A circuit according to claim 1, wherein the voltage/current converter also including a common-mode voltage control circuit means at the two inputs of the differential transresistance amplifier.

3. A circuit according to claim 2, wherein the common-mode voltage control circuit means includes:

a pair of CMOS transistors having their sources connected to a polarising voltage supply, their drains connected to the two inputs of the differential transresistance amplifier, and their gates connected to a feedback control circuit which is arranged to drive the pair of CMOS transistors so as to keep a common-mode voltage at the two inputs of the transresistance amplifier at a substantially constant value.

4. A circuit according to claim 3, wherein the feedback control circuit is arranged to drive the pair of CMOS transistors so as to keep the common-mode voltage at the two inputs of the transresistance amplifier substantially equal to the difference between a voltage of the polarising supply and a saturation voltage drop between each drain and source of the pair of CMOS transistors.

5. A circuit according to claim 4, wherein the feedback control circuit includes:

a circuit for measuring the variations of the common-mode voltage, a generator circuit for supplying a reference voltage for the common-mode voltage, and a control amplifier which has first and second inputs connected to the measuring circuit and to the generator circuit and is arranged to drive the pair of CMOS transistors in a manner such that the voltage at the two inputs of the transresistance amplifier between its first and second inputs tends to be cancelled out.

6. A circuit according to claim 5, wherein the measuring circuit includes two CMOS transistors having their drains connected to the polarizing voltage supply, their sources connected together and the connected sources connected to a current generator for generating a current and their gates connected to the drains of the pair of and to the first input of the control amplifier, CMOS transistors.

7. A circuit according to claim 6, wherein the generator circuit includes:

a first transistor constituting a replica of one of the pair of CMOS transistors and having its source connected to the polarizing voltage supply and a second transistor constituting a replica of one of the two CMOS transistors and having its drain connected to a polarization voltage source and its source connected to the current generator whose intensity is substantially equal to that of the first current generator, the second transistor being connected to the first transistor by means of a circuit for generating a polarizing voltage.

* * * * *